United States Patent
Domb et al.

[11] Patent Number: 5,919,835
[45] Date of Patent: Jul. 6, 1999

[54] BIODEGRADABLE POLYMER BLENDS FOR DRUG DELIVERY

[75] Inventors: Abraham J. Domb; Manoj Maniar; Andrew S. T. Haffer, all of Baltimore, Md.

[73] Assignee: Massachusetts Institute of Technology, Cambridge, Mass.

[21] Appl. No.: 07/995,952

[22] Filed: Dec. 23, 1992

Related U.S. Application Data

[63] Continuation of application No. 07/648,927, Feb. 1, 1991, abandoned.

[51] Int. Cl.$^6$ .................................................. A61F 2/02
[52] U.S. Cl. ..................... 523/113; 525/411; 525/415; 525/450; 424/422; 424/426
[58] Field of Search ................................ 424/422, 426, 424/428; 514/469; 525/411, 415, 450; 523/113

[56] References Cited

U.S. PATENT DOCUMENTS

| | | |
|---|---|---|
| 4,522,804 | 6/1985 | Dunn . |
| 4,757,128 | 7/1988 | Domb et al. . |
| 4,764,364 | 8/1988 | Heller et al. . |
| 4,789,724 | 12/1988 | Domb et al. . |
| 4,841,968 | 6/1989 | Dunn et al. . |
| 4,857,311 | 8/1989 | Domb et al. . |
| 4,863,457 | 9/1989 | Lee . |
| 4,886,870 | 12/1989 | D'Amore et al. . |
| 4,888,176 | 12/1989 | Langer et al. . |
| 4,891,225 | 1/1990 | Langer et al. . |
| 4,997,904 | 3/1991 | Domb . |
| 5,629,009 | 5/1997 | Laurencin et al. . |

OTHER PUBLICATIONS

Leong, et al., J. Med. Biomed. Mater. Res. 19, 941 (1985).
Leong, et al., J. Med. Biomed. Mater. Res. 20, 51 (1986).
Rosen, et al., Biomaterials 4, 131 (1983).
Kern, et al., Journal of Polymer Science XV. 183–192 (1955).
Gesner, et al., Polyblends 10, 794.
Dobry, et al., Journal of Polymer Science 2, 90, (1947).
Paul, et al., Polymer Blends Edited by D.R. Paul et al. 1, 1 (1978).
Pitt, et al., Proceed. Intern. Symp. Control. Rel. Bioact. Mater., 14, 75, (1987).

*Primary Examiner*—Raj Bawa
*Attorney, Agent, or Firm*—Arnall Golden & Gregory, LLP

[57] ABSTRACT

Blends of polymers having properties distinct from the individual polymer components and that are suitable for use as carriers of pharmaceutically active agents, are prepared from two or more polyanhydrides, polyesters or mixtures of polyanhydrides and polyesters. The blends have different properties than the polymers used to prepare the blends, providing a means for altering the characteristics of a polymeric matrix without altering the chemical structure of the component polymers. Blends of various polyanhydrides, polyesters, and polyanhydrides and polyesters, containing pharmaceutically active agents, are prepared using solvent mixing or melt mixing procedures. It has been discovered that the rate of release of the agent from the blends is different than the rate of release from the individual polyanhydride and polyester polymer components, being a function of the blend composition

12 Claims, 2 Drawing Sheets

BIODEGRADABLE POLYMER BLENDS FOR DRUG DELIVERY

This is a continuation of application Ser. No. 07/648,927 filed on Feb. 1, 1991, now abandoned.

BACKGROUND OF THE INVENTION

This invention is in the area of biodegradable polymer blends for use as carriers of pharmaceutically active agents.

Many drugs useful for the treatment of disease that are administered in an unmodified form fail to reach the target organ in an effective concentration, or are not effective over a length of time due to facile metabolism. This lack of effectiveness of the drug can result from a number of factors, including acid hydrolysis in the stomach, inability of the drug to cross membranes such as the blood brain barrier, enzymolysis of the compound, including deactivation of the drug in the liver prior to reaching the target organ, and even simple degradation or undesirable reaction of the drug in the cell or blood. In order to avoid these problems and achieve effective concentrations of drugs at the target organs, the drug is usually combined with a carrier that is biocompatible and biodegradable Suitable carriers for drug incorporation range in size from small molecules to macromolecules, including high molecular weight polymers. Polymeric devices can be used to release drug at a specific location at a controlled rate over a period of time. The most desirable polymeric matrix for drug delivery is one that is hydrophobic, stable, strong, flexible, soluble in organic solutions, has a low melting point, and degrades linearly over time in an aqueous environment. Polyanhydrides are useful for controlled drug delivery because they degrade uniformly into non-toxic molecules that are non-mutagenic, non-cytotoxic, and non-inflammatory. Further, the release rates of polyanhydride fabricated devices can be altered over a thousand-fold by simple changes in the polymer backbone. Each class of polymers has a different degradation profile, as well as other properties. It is difficult to predict if different classes of polymers can be combined to form a uniform, stable blend, and whether it will have desirable properties, including both mechanical properties and release properties.

Macroscopically uniform, single-phase, polymer—polymer blends, also referred to as polyblends, have been prepared from miscible or compatible polymer solutions for use in a variety of nonmedical applications, including in the coatings industry. However, attempts to improve the properties of varnishes and paints by blending various polymer constituents have often been frustrated by the incompatibility of the polymers. This incompatibility is manifested by the formation of films that are not homogeneous but are turbid or opaque and possess mechanical properties that are inferior to films of the separate polymer constituents.

The problems encountered by the coatings industry in their attempts to develop effective polymer blends illustrates a characteristic property of macromolecules. In general, if a polymer mixture possesses properties analogous to those expected for a single-phase material, the mixture is considered as a blend. In most instances, the critical property will be the transition temperature; a polymer blend with a single melting temperature will be classified as miscible or compatible. If the polymer mixture does not exhibit a single transition temperature, then the two polymers when mixed will often show properties of incompatibility, including nonuniformity of mixture, opacity, and separation under certain conditions.

Probably the most widely used method of determining polymer—polymer miscibility is the mutual-solvent approach, wherein an equal mixture of two polymers is dissolved at low to medium concentration in a mutual solvent. The mixture is then allowed to stand, usually for one to two days. Miscibility is considered to prevail if phase separation does not occur during this time; if phase separation does occur, the two polymers are considered immiscible.

The mutual solvent approach was first used in the field of paints and lacquers. Dobry and Boyer-Kawenoki, *J. Polym. Sci.* 2, 90 (1947), reported a study involving 78 mixtures of polymers made from 14 different polymers dissolved in 13 solvents. They concluded that most polymers show separation indicative of the immiscibility or incompatibility. Further, it was determined that when two polymers are incompatible in one solvent, they are generally incompatible in other solvents. The researchers also found that although molecular weight of the polymers is of great importance to the issue of miscibility there is no obvious relationship between the compatibility of two polymers and the chemical nature of their monomers. Additionally, the similarity of the principal chain of the polymer is not sufficient to insure miscibility of two polymers. Based on these conclusions, it is clear that miscibility of two polymers is unlikely and very hard to predict.

It is therefore an object of the present invention to provide compatible blends of biodegradable polymers for use as matrix materials in delivery devices, as well as methods for their preparation.

It is a further object of the present invention to provide compatible polymer blends that provide uniform release of incorporated substance over an extended period of time.

SUMMARY OF THE INVENTION

Blends of polymers having properties distinct from the individual polymer components and that are suitable for use as carriers of pharmaceutically active agents, are prepared from two or more polyanhydrides, polyesters or mixtures of polyanhydrides and polyesters. The blends have different properties than the polymers used to prepare the blends, providing a means for altering the characteristics of a polymeric matrix without altering the chemical structure of the component polymers.

As demonstrated by the examples, blends of polyanhydrides, polyesters, and polyanhydrides and polyesters, containing pharmaceutically active agents, are prepared using solvent mixing or melt mixing procedures. It has been discovered that the rate of release of an incorporated biologically active agent from the blends is different than the rate of release from the individual polyanhydride and polyester polymer components, being a function of the blend composition: both polymer composition and ratio of constituent polymers.

DETAILED DESCRIPTION OF THE INVENTION

Figure 1:
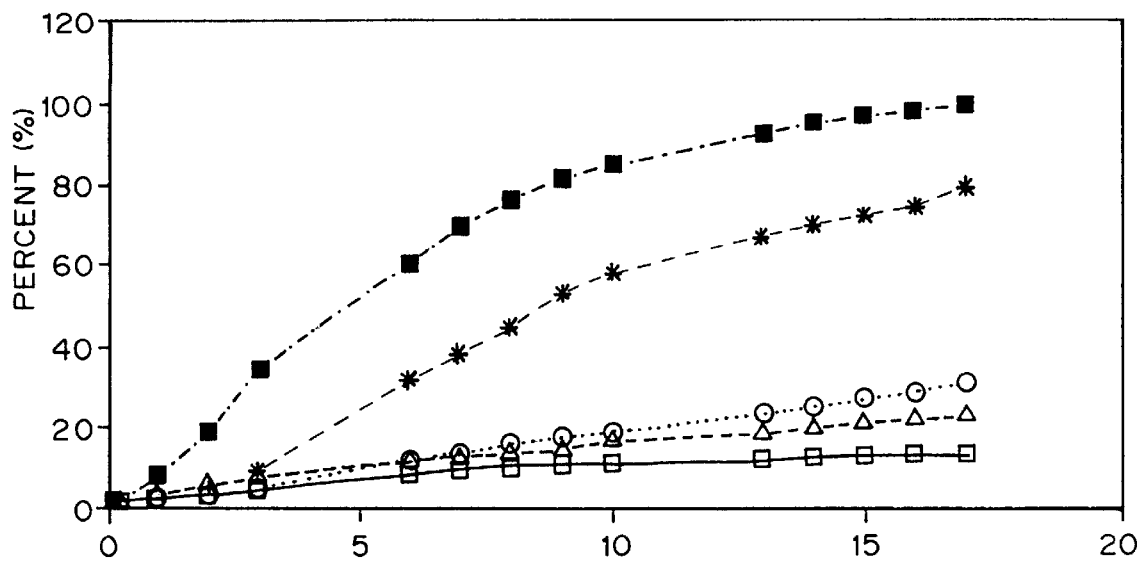
FIG. 1 is a graph of the percent of marcaine HCl released from poly(lactic acid) [PLA] (—squares—), PLA:poly (sebacic anhydride) [PSA] (90:10) (—triangles—), PLA:PSA (80:20) (—0—), PLA:PSA (70:30) (—*—) and PLA:PSA (50:50)(—dark squares—) over time (days) at 37° C. in 0.1 M phosphate buffer, pH 7.4.

The method described herein is a technique for the preparation of blends of polyanhydride and polyester polymers into which pharmaceutically active agents, for example, antibiotics, anti-inflammatories, anesthetics, antivirals, antifungals, antihypertensives, antiarrhythmics, or neuroactive agents, are incorporated for subsequent release in vivo. Two or more polymers are considered miscible and compatible if, when blended in a mutual solvent or solvent mixture, they form a homogeneous solution for at least one day at room temperature (between 20 and 30° C.).

It has been discovered that homogeneous blends of polyanhydrides, polyesters and mixtures thereof can be prepared using either the solvent mixing or melt mixing procedures, both well known to those skilled in the art. Homogeneity of the polymer blend is essential for uniform release of incorporated drugs to occur in vivo. If the polymers forming the matrix are not compatible or miscible with each other or the incorporated drug, a non-uniform distribution of components will result, causing the drug to be released in a random fashion.

The selection of a biodegradable polymer blend is based on the following parameters:

1. The blend forms a clear single phase solution in a mutual solvent, in general chloroform or methylene chloride;
2. The blend forms a uniform film when cast from solvent or melt compressed;
3. The blend has different thermal properties (melting point or Tg) from the original starting polymers; and
4. The blend has different release properties from the original polymers.

In addition, the blends may have differences in the physical and mechanical properties such as lower crystallinity and mechanical strength.

Blends of polymers possess different mechanical and physical properties from the original polymers. Properties such as the transition temperature, solubility, mechanical strength, and crystallinity are often altered by blending. Further, blends of biodegradable polymers degrade differently and also have different release properties than the original polymers. The blends described herein exhibit a greater overall release of pharmaceutical agent, and faster release rate, than do the original polymers.

Copolymers are a result of a chemical reaction of two or more monomers to form a polymer. Blends are a result of a physical mixture of two or more polymers. To make a copolymer, monomers must be polymerized into a copolymer. Frequently, in a blend, both polymers remain intact but physically mixed uniformly in the molecular level, with both polymers having the same type of bonds as the original polymers, i.e., an ester bond, and an anhydride bond, both biodegradable bonds. If, on the other hand, a copolymer of lactic acid and sebacic acid is prepared, one may get ester bonds between lactic acid and sebacic acid which are not readily degradable. One might not get a polymer at all because lactide and sebacic acid are not polymerizable together.

In a blend, one starts with well defined polymers which are expected not to change in the blend. For a compatible pair of polymers, any ratio and any molecular weight polymers can be mixed to form a new product. Copolymers are limited since not all ratios of monomers can be polymerized nor in a desired molecular weight.

Drug can be incorporated during the preparation of blends, but many cannot be incorporated during copolymerization at 180° C. since the drug is destroyed and can interact or interfere in the polymerization process.

Polymers for use in polymeric matrices for controlled drug delivery must be biocompatible and degrade uniformly into non-toxic molecules that are non-mutagenic non-cytotoxic, and non-inflammatory. Nonlimiting examples of polyanhydrides and polyesters that are useful in the preparation of polymer blends include polymers and copolymers of lactic acid, glycolic acid, hydroxybutyric acid, mandelic acid, caprolactone, sebacic acid, 1,3-bis(p-carboxyphenoxy) propane (CPP), bis-(p-carboxyphenoxy)methane, dodecandioic acid (DD), isophthalic acid (ISO), terephthalic acid, adipic acid, fumaric acid, azeleic acid, pimelic acid, suberic acid (octanedioic acid), itaconic acid, biphenyl-4,4'-dicarboxylic acid, and benzophenone-4,4'-dicarboxylic acid. Also suitable are polyorthoesters made from the reaction of ketene acetals and polyols using the method of Heller, J., et al., *J. Polymer Sci. Polymer Letters Ed.* 18:92 (1980), and copolymers of propylene glycol and fumaric acid (referred to below as polypropylene fumarate). Polymers can be aromatic, aliphatic, hydrophilic or hydrophobic.

The polymer blends are formed using known methods such as solvent mixing and melt mixing. In the solvent mixing procedure, the desired weight of each of the polymers to be blended is mixed in the desired amount of an appropriate organic solvent or mixture of solvents, and the polymer solutions are mixed. The organic solvent is then removed, for example, by evaporation, leaving a polymer blend residue. Drugs or additives are incorporated by dissolving or dispersing them in the blend solution prior to removal of the solvent. This method is especially useful for the preparation of polymer blends or incorporation of drugs that are sensitive to elevated temperatures.

In the melt mixing procedure, the polymers are melted together or brought separately to its respective melting temperature and then mixed with each other for a short time, for example, for about two minutes. The blend is then allowed to cool to room temperature. Drugs or additives are incorporated by dissolving or dispersing them either in the blend solution or in the individual melt solutions prior to blending. This procedure is especially useful for the preparation of polymer blends in which at least one of the polymers or the drug to be incorporated is not very soluble in organic solvents.

The transition temperature is a critical property of the blend. Miscibility or compatibility of blended polymers is indicated by a single melting temperature of the blend. A blend with two or more melting temperatures indicates immiscibility of the polymers and a multi-phase material. The transition temperature or temperatures of the blend can be measured by differential scanning calorimetry (DSC).

The formation of a single phase solution following the mixing of polymers indicates that the polymers are compatible and miscible. This property is essential to the formation of a polymer matrix with suitable aqueous erosion kinetics for use in drug delivery. The polymers are considered insoluble if phase separation occurs in less than one day at 20–30° C. after mixing.

An advantage of the polymer blends prepared according to this method is that they are generally more pliable than the starting polymers. A blend with high pliability is easy to manipulate and not likely to break during preparation into forms such as tablets or capsules which can be administered to a patient. Polymer blends prepared according to this method also generally have lower melting temperatures and heat capacities than those of the individual polymers, due to a decrease in crystallinity of the material. This allows for the incorporation of heat sensitive drugs that could not withstand the heat required to melt the individual component polymers. The molecular weights and viscosities of the blends are typically an average of the molecular weights and viscosities of the component polymers.

The present invention will be further understood by reference to the following non-limiting examples.

EXAMPLE 1

Miscibility of polymers in solution.

The phase separation solution miscibility method, described in Dobry and Boyer-Kawenoki, *J. Polym. Sci.* 2, 90 (1947), and *Polymer—Polymer Miscibility* p. 159, Olabisi, O. Robeson, L. M., and Shaw, M. T. editors, (Academic Press, New York, 1979), was used to determine the miscibility of biodegradable polymers. Dichloromethane solutions of polymers to be tested were mixed, and the mixture examined after one and three days. A uniform clear solution indicated miscible polymers; separation into layers indicated immiscibility.

20% w/v solution of polymers in dichloromethane were prepared as stock solutions. Two solutions were mixed in equal volumes to form blends. The vials were kept at room temperature and examined at 0, 24 and 72 hours to determine miscibility. A uniform clear solution indicated miscible polymers. Two layers indicated immiscibility. If separate layers formed, IR spectra were obtained to determine the composition of each layer, and then a sample of each layer was evaporated to dryness, and the formed film examined and analyzed by $^1$H-NMR.

The following polymers were mixed in this study. The Mw is weight average molecular weight.

Polyanhydrides
poly(sebacic anhydride) [PSA], Mw-54,900
poly(fatty acid dimer-SA) [P(FAD-SA)](1:1}, Mw-42,000
poly(CPP-SA) (20:80), Mw-56,700
poly(ISO-CPP)20:80, MW-18,900

Polyesters
poly(3-hydroxybutyric/3-hydroxyvaleric acid) (1:3) [PHB], Mw-150,000
polycaprolactone [PCL]. Intrinsic viscosity 1.14 dl/g in CHCl$_3$ at 30° C.
polycaprolactone [low PCL], Mw-2,000
poly(DL-lactic acid) [low PLA], Mw-2,000
poly(DL-lactic acid) [PLA], Mw-44,000
poly(L-lactic acid) [L-PLA], intrinsic viscosity 0.70 dl/g in CHCl$_3$ at 30° C.
poly(lactic-glycolic acid) (65:65) [PLA-GA], intrinsic viscosity 0.65 dl/g in HFIP at 30° C.
poly(mandelic acid) [PMA], Mw-1,800
poly(propylene fumarate) [PPF], Mw-2,400
poly(orthoester) [POE]- intrinsic viscosity 0.28 dl/g in CHCl$_3$ at 25° C., made from the reaction of ketene, acetal and polyols by the method of J. Heller, et al. *J. Polymer Sci. Polymer Lett. Ed.* 18,82 (1980), the teachings of which are incorporated herein by reference. The results are summarized in Table 1.

TABLE 1

Polymer-Polymer miscibility using the solvent separation method:

| Mixtures | Separation | I.R. Characteristics and Classification | Film Appearance |
|---|---|---|---|
| P(SA) + PHB | homogeneous | The IR for this homogeneous solution shows properties of both components. | Uniform opaque |
| P(SA) + PCL | 2 distinct layers 50:50 | Both IR are quite similar, showing that some interaction has taken place. | two separate layers |
| P(SA) + PLA low Mw | homogeneous | Common characteristics of each polymer are shown on the IR spectra. | Uniform opaque |
| P(SA) + P(LA-GA) 65:35 | 2 distinct layers 50:50 | Top: This layer determined to be p(SA) by IR. Bottom: This layer is p(LA-GA) 65:35, but looking at CH and carbonyl Region shows extra peaks. | Top: opaque Bottom: clear |
| P(SA) + p(Mandelic) | homogeneous | Components of both indicated by IR. | Uniform |
| P(SA) + POE | homogeneous | Components characteristic of each polymer are indicated on IR. | Uniform |

TABLE 1-continued

Polymer-Polymer miscibility using the solvent separation method:

| Mixtures | Separation | I.R. Characteristics and Classification | Film Appearance |
|---|---|---|---|
| P(SA) + L(PLA) | 2 distinct layers 50:50 | Top: IR shows top to be P(SA). Bottom: Bottom is L-PLA but again we see an extra peak in CH and Carbonyl Region of Spectra. | Top: opaque Bottom: clear |
| P(CPP-SA) (20:80) + HMW PCL | 2 distinct layers | Top: shown to be P(CPP-SA) 20:80 Bottom: PCL, but has some characteristics in CH and Carbonyl of P(SA) spectra. | two separate layers |
| P(CPP-SA) 20:80 + PLA Low Mw | homogeneous | Components of both indicated by IR. | Uniform |
| P(CPP-SA) 20:80 + P(LA-GA) 65:35 | 2 distinct layers | Top: P(CPP-SA) 20:80 is the top layer Bottom: PLA + characteristics in CH + $CO_2$ of P(CPP-SA) 20:80 | two separate layers |
| P(CPP-SA) + P(Mandelic) | homogeneous | Components of both indicated by IR. | Uniform |
| P(CPP-SA) 20:80 + POE | homogeneous | Components of both indicated by IR. | Uniform |
| P(CPP-SA) 20:80 + L-PLA | 2 distinct layers | Top: P(CPP-SA) 30:30 is the top layer Bottom: L-PLA on the bottom layer | two separate layers |
| P(FAD-SA) 1:1 + PHB | homogeneous | IR corresponds to both polymers | Uniform opaque |
| P(FAD-SA)1:1 + PCL | cloudy mixture | Solution was cloudy so IR was taken off top and bottom layers, both were the same, and the IR's had peaks common to both components. | no film |
| P(FAD-SA)1:1 + PLA Low MW | homogeneous | IR corresponds to both polymers | translucent |
| P(LA-GA)65:35 + P(FAD-SA)1:1 | 2 distinct layers 50:50 | Top: Top layer as indicated by IR is only P(FAD-SA)1:1 Bottom: Mostly characteristic of P(LA-GA)65:35 with small change in CH stretch due to P(FAD-SA)1:1. | Top:translucent Bottom: clear |
| P(FAD-SA)1:1 + P(Mandelic) | homogeneous | IR corresponds to both polymers. | Uniform opaque |
| P(FAD-SA)1:1 + POE | homogeneous | IR corresponds to both polymers. | Uniform opaque |
| P(FAD-SA)1:1 + L-PLA | total separation 50:50 | Top: IR shows the top layer to be only P(FAD-SA)1:1 Bottom: This layer is distinctly L-PLA with characteristics of P(FAD-SA)1:1. | Top:translucent Bottom: clear |
| PHB + PCL | homogeneous | IR - esters. | clear, uniform |
| PHB + PLA Low Mw | homogeneous | IR - esters. | clear, uniform |
| PHB + P(LA-GA)65:35 | homogeneous | IR - esters. | clear, uniform |
| PHB + P(Mandelic) | homogeneous | IR - esters. | clear, uniform |
| PHB + POE | homogeneous | IR - esters. | clear, uniform |
| PHB + L-PLA | homogeneous | IR - esters. | clear, uniform |
| POE + PCL | homogeneous | IR - esters. | clear, uniform |
| POE + P(LA-GA) 65:35 | homogeneous | IR - esters. | clear, uniform |
| POE + P(Mandelic) | homogeneous | IR - esters. | clear, uniform |
| POE + L-PLA | 2 distinct layers | Top: Top layer is PLE with traits of L-PLA in the $CO_2$ Region. Bottom: Bottom layer is L-PLA with CH character of POE. | two layers |
| P(SA) + PCL Low Mw | homogeneous | IR corresponds to both polymers. | uniform opaque |
| P(FAD-SA) + PCL Low Mw | homogeneous | IR corresponds to both polymers. | uniform opaque |

TABLE 1-continued

| | Polymer-Polymer miscibility using the solvent separation method: | | |
|---|---|---|---|
| Mixtures | Separation | I.R. Characteristics and Classification | Film Appearance |
| PSA + P(CPP-SA) 20:80 | homogeneous | IR - polyanhydrides. | uniform opaque |
| PSA + P(FAD-SA)1:1 | homogeneous | IR - polyanhydrides. | opaque uniform |
| P(CPP-SA) 20:80 + P(FAD-SA)1:1 | homogeneous | IR - polyanhydrides. | opaque uniform |

The solutions that are homogenous have IR spectra that reflect both components. For the samples that showed separation, the IR of the top layer indicated only polyanhydride. The bottom layer primarily contains polyester, but also shows characteristic peaks for polyanhydrides. $^1$H-NMR is used to determine the miscibility of the polyanhydride in the polyester layer. NMR confirmed that polyanhydride is always in the top layer, and the polyester is always on the bottom. Films of the PSA and P(CPP-SA), as well as their blends with polyesters, are opaque, while films of the polyesters and their blends are clear.

The following conclusions can be drawn from this data: (1) two or more soluble anhydride polymers are miscible and form blends; (2) two or more of the following polyesters are miscible: lactide and glycolide polymers, hydroxybutyric acid polymers, polyorthoesters, mandelic acid polymers, poly (propylene fumarate) and polycaprolactones; (3) high molecular weight lactide and glycolide polymers and polycaprolactones are not miscible with anhydride polymers; (4) poly(orthoesters) are not miscible with L-PLA; (5) low molecular weight polymers, up to 5,000 Mw, of lactide and glycolide, mandelic acid, propylene fumarate, and caprolactone are miscible with anhydride polymers; (6) poly(orthoesters) and hydroxybutyric acid polymers are miscible with anhydride polymers.

EXAMPLE 2

Blends of low molecular weight poly(lactic acid) and poly(sebacic anhydride).

Blends were prepared by mixing a 20% w/v dichloromethane solution of low molecular weight PLA (Mw=1,750) with various amounts of a 20% dichloromethane solution of PSA to form homogeneous solutions. After solvent evaporation, white, cotton like, PLA:PSA blends containing 5, 10, 20, 30, and 50% w/w PSA were obtained.

The IR spectra show peaks of PLA and PSA according to the PSA content in the polymer blend (PLA peaks at 2990, 2940, and 1750; PSA peaks at 2830, 1920, 1810, and 1740 cm$^{-1}$).

The molecular weight of the blends were in the range of 21,000 to 29,000.

EXAMPLE 3

Release of bupivacaine (marcaine) from polymer blends.

The drug bupivacaine hydrochloride was mixed into melted blends of various polymers and cast into a rubber mold to form a 3×5×10 mm bar. These were used for in vitro release studies into 0.1 M phosphate buffer, pH 7.4, at 37° C. The results are summarized in FIG. 1.

The blends show a near constant release of drug. Drug release from the PLA can be enhanced by blending with PSA. In general, increasing the drug loading of the PSA increases the drug release in vitro. For example, over a period of 17 days, 100% of bupivacaine was released from a PSA:PLA (1:1) blend whereas only 13% of bupivacaine was released from pure PLA.

EXAMPLE 4

Blends of aliphatic polyanhydrides.

Aliphatic polymers of the following diacids: adipic acid (AA), suberic acid (SU), sebacic acid (SA) azelaic acid (AZ) and 1,12-dodecanedicarboxylic acid (DD) were prepared by melt polycondensation. The polymers were melt or solution mixed in a 1:1 weight ratio to form uniform blends. The physical properties of the various blends prepared by melt mixing are summarized in Table 2.

TABLE 2

| Polyblends of Aliphatic Homopolymers | | | | | |
|---|---|---|---|---|---|
| POLYMERS | DSC'S | HEAT CAPACITY | VISCOSITY | MW | COMMENTS |
| HOMOPOLYMER | | | | | |
| p(AA) | 71 | 67 | 0.19 | 14,900 | waxy, brittle |
| p(AZ) | 83 | 78 | 0.68 | 75,300 | waxy, brittle |
| p(SU) | 69 | 72 | 0.50 | 44,500 | waxy, brittle |
| p(DD) | 93 | 72 | 0.65 | 65,800 | waxy, brittle |
| p(SA) | 81 | 91 | 0.39 | 37,700 | waxy, brittle |
| BLENDS (1:1) | | | | | |
| p(AA) + p(SA) | 49 | 66 | 0.29 | 27,600 | cheese-like soft |
| p(AA) + p(DD) | 62 | 48 | 0.41 | 40,200 | pliable, waxy |
| p(SU) + p(SA) | 60 | 48 | 0.40 | 46,500 | hard, waxy |
| p(SU) + p(DD) | 62 | 45 | 0.52 | 48,400 | hard, waxy |
| p(AZ) + p(SA) | 60 | 41 | 0.52 | 46,200 | hard |
| p(AZ) + p(DD) | 56 | 44 | 0.55 | 51,200 | hard, waxy |

The blends of the homopolymers melt at lower temperatures and are less crystalline (as estimated from the lower heat capacities) as compared to the respective homopolymers. The blends show a single peak in the DSC chromatography, indicating a single compound. All blends show a single phase solution when dissolved in dichloromethane. The blends are less brittle than the separate polymers alone.

These changes in the polymer properties are advantageous for device fabrication in which a lower melting temperature is necessary for the incorporation of heat sensitive drugs. In addition, these pliable polymer blends are easy to manipulate and will not break during handling. The molecular weight of the blends are a combination of the starting polymer, indicating no change in the molecular weight properties during blending. The blends prepared by the solution method possess similar properties. For example, the blend of p(SA) and p(AA) in a 1:1 weight ratio was a soft waxy material that melted at 46° C.

EXAMPLE 5

Blends of poly(FAD), a liquid polymer, and poly (sebacic anhydride).

Poly(fatty acid dimer), p(FAD), is a liquid polymer made of a fatty acid dimer, 36 Pripol™ 1009 (Unichem), synthesized according to U.S. Ser. No. 07/467,635 by Abraham Domb, the teachings of which are incorporated herein. Poly(sebacic anhydride), p(SA), is a solid, brittle polymer that melts at 81° C. When these two polymers are combined into a blend, a uniform, pliable material is obtained. The characterization of various blends formed by these polymers is summarized in Table 3.

TABLE 3

Blends of poly(PAD) and poly(SA)

| POLYMERS | DSC'S | HEAT CAPACITY | VISCOSITY | FILM PROPERTIES |
|---|---|---|---|---|
| HOMO-POLYMERS | | | | |
| p(FAD) | no peak | — | 0.24 | viscous, sticky liquid |
| p(SA) | 81 | 91 | 0.43 | milky appearance, waxy solid, forms very brittle films |
| BLENDS + (RATIO) | | | | |
| p(FAD) + p(SA) 1:1 | 62 | 31 | 0.37 | clear, waxy, flexible film |
| p(FAD) + p(SA) 2:1 | 45 | 28 | 0.32 | sticky clear film |
| p(FAD) + p(SA) 1:2 | 70 | 51 | 0.40 | milky cheesecake |

Blends of these polymers produced clear, flexible, and uniform films. $^1$H-NMR analysis of various samples across a film indicated a uniform distribution of the two polymers. The blends form a single phase solution in dichloromethane.

EXAMPLE 6

Blends of anhydrides and anhydride copolymers.

Various copolymers of aliphatic and aromatic diacids were blended by melt mixing at 180° C. for 60 seconds. The characterization of the blends is summarized in Table 4.

TABLE 4

Blends of various anhydride copolymers

| POLYMERS | MP °C. | VISCOSITY dl/g | MW | PROPERTIES |
|---|---|---|---|---|
| HOMOPOLYMERS + COPOLYMERS | | | | |
| P(CPP-SA) (2:8) | 72–74 | 0.65 | 52,000 | pliable |
| P(SA) | 81–83 | 0.70 | 55,000 | brittle |
| P(FAD-SA) (1:1) | 64–68 | 0.60 | 48,000 | flexible, clear, |
| P(CPP-ISO) (2:8) | 110–115 | 0.31 | 22,400 | tough, clear |
| P(TA-ISO) (2:8) | 110–115 | 0.22 | 17,010 | brittle, clear |
| BLENDS OF: | | | | |
| P(CPP-SA) (2:8) + P(SA) | 58–63 | 0.60 | 48,100 | brittle |
| P(FAD-SA) 1:1 + P(SA) | 73–79 | 0.55 | 46,700 | pliable, clear |
| P(FAD-SA)(1:1) + P(CPP-ISO) (2:8) | 65–70 | 0.38 | 26,900 | soft, opaque |
| P(CPP-ISO) (2:8) + P(TA-ISO) (2:8) | 108–120 | 0.26 | 19,100 | brittle, clear |
| P(SA) + P(CPP-ISO) (2:8) | 40–45 | 0.42 | 33,400 | sticky, clear |
| P(SA) + P(TA-ISO) (2:8) | 44–50 | 0.48 | 36,400 | sticky, soft, clear |

All of the mixtures of these polymers and copolymers formed uniform blends. The blends had a single transition temperature and formed clear films. The melting temperatures were lower than the melting temperatures of the starting polymers. The blends of P(SA) and the aromatic copolymers melted at significantly lower temperature and were softer and more transparent than the starting polymers. All blends yielded uniform clear films by melt compression, indicative of a single product. The molecular weights and viscosities of the blends were an average of separate polymers, with a slight decrease in molecular weight for the blends containing the aromatic copolymers.

Blends of aromatic polyanhydrides and homo- or copolymers of aliphatic acids were also studied. The aromatic homopolymers are insoluble and melt at temperatures of about 250° C.

The aromatic homopolymer p(CPP) was mixed with p(SA) (Mw=56,000, melting point (MP) 81° C. in a 1:1 or 1:4 weight ratio by melting the two polymers together at 220° C. for about ten minutes until a homogeneous clear melt was obtained. These conditions were used because of the high melting point and the insolubility of the aromatic polymers. The 1:1 and 1:4 mixtures of p(CPP) and p(SA) melted at 65° C. and 110° C. and had molecular weights of 5,600 and 22,000, respectively. The products were analyzed by $^1$H-NMR to determine chemical interactions. The spectra for the p(CPP)+p(SA) blends show new peaks (small triplets at 7.8 and at 2.2) for both compositions that indicate polymer interactions to form new copolymers.

These results suggest that blends of high melting polyanhydrides cannot be prepared without initiating a copolymerization reaction.

EXAMPLE 7

Blends of lactic acid polymers and polyanhydrides.

Various polyanhydrides (p(SA), p(FAD), and p(CPP-SA) (2:8) and p(CPP-SA)(1:1)), were blended with poly(lactic acid) or poly(lactic-glycolic acid) (1:1) by the melt or solvent mixing methods. Both types of polymers had a high molecular weight in the range of 40,000 and 70,000.

In a typical experiment, 0.5 g of p(CPP-SA) (1:1) was mixed with 0.5 g of poly(lactic acid) at 180° C. for 1 minute, cast between Teflon™ coated glass plates and left to cool to room temperature. A clear but not uniform film was obtained. The DSC of the blends show two distinct peaks for the polyanhydrides at 60–80° C. and for the polyester at 130–170° C., indicative of incompatibility of the polymers. The film uniformity was further determined by infrared spectroscopy (IR) as follows. The polyanhydride has typical anhydride peaks at 1740 and 1805 cm-1 and poly(lactic acid) has a typical ester peak at 1720 cm-1. A uniform film should show the same anhydride and ester peak ratio across the blend films. All blend films made of the above polyanhydrides and poly(lactic acid) or poly(lactic-glycolic acid) (1:1) blends were not uniform as shown by the differing ratios of anhydride and ester peaks of the IR spectra of various samples of the blend films. Similar results were obtained when poly(caprolactone), intrinsic viscosity 1.14 dl/g as determined in $CHCl_3$ at 30° C. was blended with polyanhydrides under the same conditions. It appears that high molecular weight lactide polymers and caprolactones do not form a homogeneous blend with polyanhydrides.

EXAMPLE 8

Blends of polyorthoesters and polyanhydrides.

Polyorthoester [POE] was blended with several polyanhydrides by the melt or solvent mixing methods. The blends are characterized in Table 5.

TABLE 5

Blends of polyorthoesters and polyanhydrides

| POLYMERS | MP | VISCOSITY | MW | COMMENTS |
|---|---|---|---|---|
| HOMOPOLYMERS | | | | |
| POE | 80–84 | 0.15 | 13,040 | transparent, flexible |
| PSA | 81–83 | 0.32 | 22,900 | brittle, opaque film |
| P(FAD) | liquid | 0.22 | 20,025 | liquid |
| BLENDS | | | | |
| POE:PSA(1:1) | 53–56 | 0.22 | 6,260 | uniform, flexible |
| POE:P(FAD) (4:1) | 43–47 | 0.25 | 13,700 | transparent, flexible |

POE and polyanhydrides formed uniform blends with a single melting temperature that is lower than that of the respective polymers. The blends form uniform flexible films with a uniform distribution of the polymers as determined by IR analysis (same peak ratio for anhydride and ester absorbances).

EXAMPLE 9

Blends of polyanhydrides and various polyesters.

Poly(sebacic anhydride), PSA, was blended with low molecular weight poly(caprolactone), poly(hydroxybutyric acid), and poly(propylene fumarate). The polymers were melt mixed, in a 1:3 p(SA):polyester weight ratio, at 180° C. for 60 seconds and cast into a film. Opaque cloudy but strong films were obtained from these compositions, indicative of partial blending.

The polymers were uniformly distributed in the blends as evidenced by the same peak ratios for anhydride and ester absorbances of the IR spectra of various specimens of the films.

EXAMPLE 10

Drug Release from Polymers and Blends.

A. Tablets of various polyanhydride blends (PSA:PFAD (2:1); PDD:PFAD (2:1); PDD:PSU (1:1) and PSU:PSA (1:1)) containing 5% indomethacin were prepared by melt mixing indomethacin in the molten blend and casting the combination into a 10×5×3 mm rubber mold. The devices were placed in 20 ml of 0.1 M phosphate buffer at pH 7.4 at 37° C. The solution was replaced with fresh buffer solution every day and the buffer analyzed for indomethacin content by HPLC using the method described in USP Vol. 21.

Figure 2:
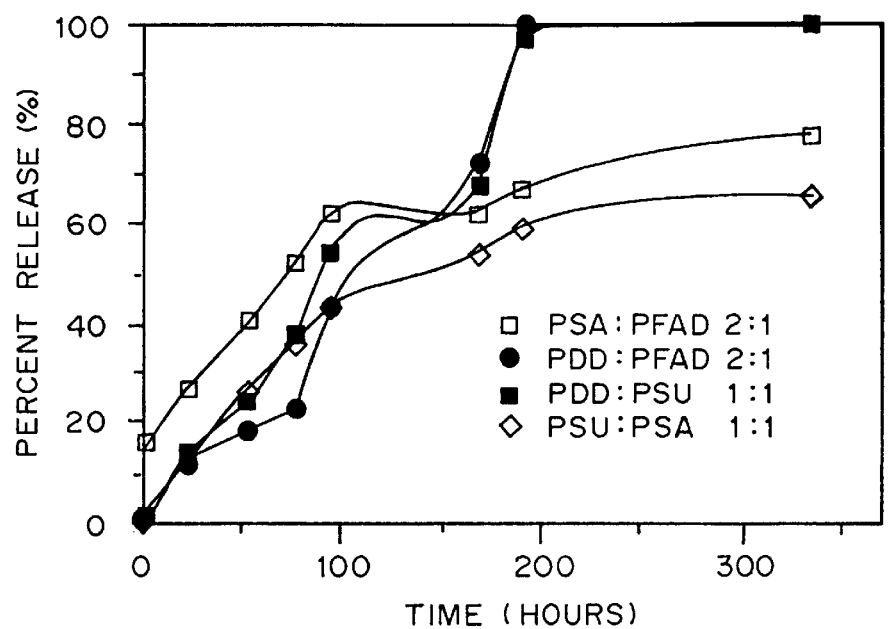
FIG. 2 is a graph of the percent of indomethacin released from poly(sebacic acid)[PSA]:poly(fatty acid dimer) (36 Pripol™1009, Unichema) [PFAD] (2:1) (—squares—), poly (1,12-dodecanedicarboxylic acid)[PDD]:PFAD (2:1)(—dark circles—), PDD:poly(suberic acid)[PSU] (1:1)(—dark squares—), and PSU:PSA (1:1)(—diamonds—) polyanhydride blends over time (hours) at 37° C. in 0.1 M phosphate buffer, pH 7.4.

The results are shown in FIG. 2. The greatest release was from the PDD:PSU(1:1) and PSU:PSA(1:1) blends. The lowest release was from the PDD:PFAD(2:1) blend.

B. The release of triamcinolone from PLA-poly(mandelic acid) blend was studied. Poly(mandelic acid) was prepared by melt condensation. The methyl ester of mandelic acid (PME) was mixed with p-toluene sulfonic acid and left for 24 hours at 140° C. and 6 hours at 180° C. under 0.5 mm vacuum. The resulting polymer has a molecular weight of 2,500, and PLA has a molecular weight of 44,000. The blends were prepared by melt mixing the polymers in a 1:1 weight ratio, and 10% triamcinolone was added by melt mixing of the drug into the blend or PLA alone. Release studies from PLA and the PLA-PME blend were performed in 0.1 M phosphate buffer, pH 7.4 at 37° C. using 200 mg devices.

Figure 3:
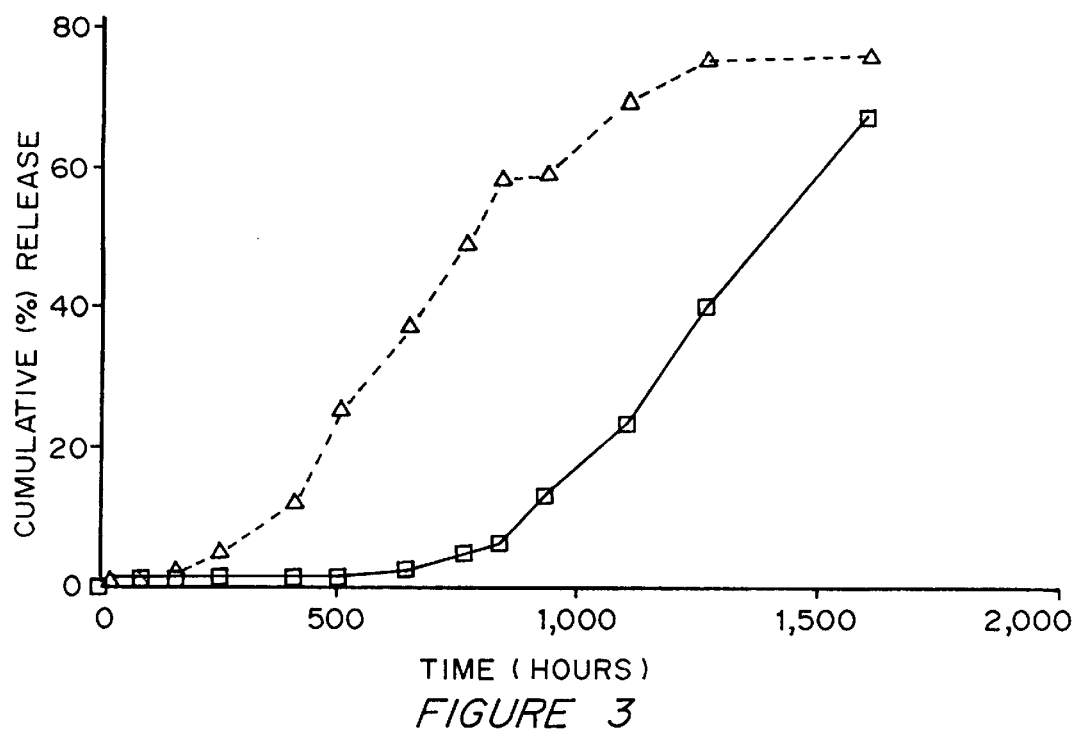
FIG. 3 is a graph of the percent of triamcinolone released from poly(lactic acid)[PLA] (—squares—) and PLA:poly(mandelic ester)[PME] (1:1)(—triangles—) blend over time (hours) at 37° C. in 0.1 M phosphate buffer, pH 7.4.

The PLA polymer released about 70% of the triamcinolone after 1600 hours with a lag time of about 800 hours, while the blend containing 50% poly(mandelic acid) released 80% of the drug after 1600 hours with a lag time of 200 hours. The results are shown in FIG. 3.

C. The release of marcaine HCL from PSA-PHB blends was also studied. PSA:PHB blends in ratios of 10:90, 20:80, and 50:50 were prepared using the solvent mix method. The PSA (Mw=54,100) and PHB (Mw=150,000) were separately dissolved in 25 ml of $CH_2Cl_2$, and the two solutions were then mixed in the ratios stated above. The solvent was removed by vacuum. Tablets containing 10% marcaine HCl were prepared by melt casting the drug into each of the three prepared blends.

Figure 4:
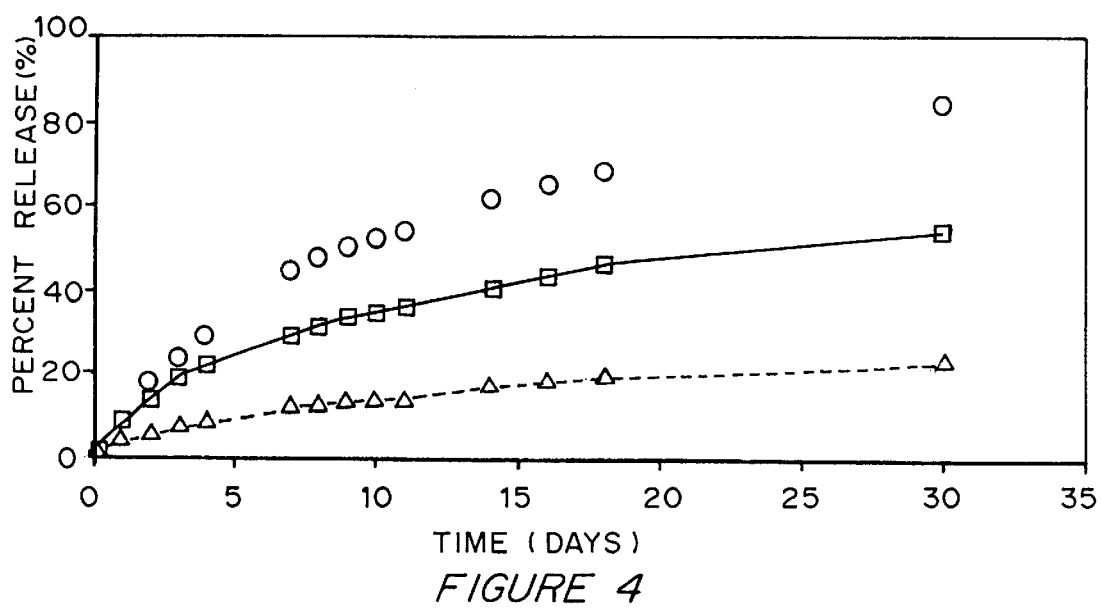
FIG. 4 is a graph of the percent of marcaine HCl released from poly(sebacic acid)[PSA]:poly(3-hydroxybutyric/3-hydroxyvaleric acid 86:14)[PHB] (20:80)(—squares—), PSA:PHB (10:90)(—triangles—), and PSA:PHB (50:50)(—O—) blends over time (days) at 37° C. in 0.1 M phosphate buffer, pH 7.4.

After 30 days, about 20% of the marcaine HCl was released from the PSA:PHB (10:90), 50% from the PSA:PHB (20:80), and 80% from the PSA:PHB (50:50). The results are shown in FIG. 4. These results suggest that the most uniform blend and the greatest marcaine HCl release occurs when the polyanhydride and polyester are blended in equal ratios.

These examples demonstrate that blends of polyanhydrides, polyesters, and polyanhydrides and polyesters can be used as effective carriers of pharmaceutical agents. Further, blends have desirable properties for use in polymeric matrices for drug delivery, including lower melting points and greater solubility than the component polymers alone. The examples also show that the blends have different release of incorporated drugs than the individual constituent polymers.

Modifications and variations of the present invention, biodegradable polyblends, will be obvious to those skilled in the art from the foregoing detailed description of the invention, and are intended to come within the scope of the following claims.

We claim:

1. A polymer blend prepared by:
   selecting two or more polymers from the group consisting of polyesters and polyanhydrides, forming a melt of the polymers by combining the polymers in molten form, determining whether the polymers are miscible by determining if phase separation occurs when the polymer blend is dissolved in a solvent in which each of the individual polymers is soluble for at least one day at a temperature between 20 and 30° C., and selecting those blends which are formed by miscible polymers, wherein the polymer blend forms a clear single phase solution in a solvent in which each of the individual polymers is soluble, forms a uniform film when cast from solvent or melt compressed, has thermal properties selected from the group consisting of glass transition temperature and melting point that are different from the original starting polymers, and releases an incorporated agent differently from the polymers forming the blend.

2. The composition of claim 1 wherein there are at least three polymers forming the blend.

3. The composition of claim 1 further comprising a pharmaceutically active agent.

4. The composition of claim 1 wherein the polyanhydrides are polymerized or copolymerized from monomers selected from the group consisting of sebacic acid, 1,3-bis(p-carboxyphenoxy) propane, 1,3-bis(p-carboxyphenoxy) methane, dodecandioic acid, isophthalic acid, terephthalic acid, adipic acid, fumaric acid, azeleic acid, pimelic acid, suberic acid (octanedioic acid), itaconic acid, biphenyl-4,4'-dicarboxylic acid, and benzophenone-4,4'-dicarboxylic acid.

5. The composition of claim 1 wherein the polyesters are polymerized from monomers selected from the group consisting of 3-hydroxybutyric acid, 3-hydroxyvaleric acid, caprolactone, lactic acid, glycolic acid, and mandelic acid, polypropylene fumarate, and polyorthoesters.

6. The composition of claim 5 wherein the poly (orthoester) is the reaction product of a ketene acetal and a polyol.

7. The composition of claim 1 wherein the blend is formed of at least one polyanhydride and one polyester.

8. The composition of claim 3 wherein the pharmaceutically active agent is selected from the group consisting of antibiotics, anti-inflammatories, anesthetics, antivirals, antifungals, antihypertensives, antiarrhythmics and neuroactive agents.

9. A method of controlled delivery of substances comprising providing a biologically active agent in a polymer blend prepared by:

forming a melt of at least two polymers selected from the group consisting of polyesters and polyanhydrides by combining the polymers in molten form, determining whether the polymers are miscible by determining if phase separation occurs when the polymer blend is dissolved in a solvent in which each of the individual polymers is soluble for at least one day at a temperature between 20 and 30° C., and selecting those blends which are formed by miscible polymers, wherein the polymer blend forms a clear single phase solution in a solvent in which each of the individual polymers is soluble, forms a uniform film when cast from solvent or melt compressed, has thermal properties selected from the group consisting of glass transition temperature and melting point that are different from the original starting polymers, and releases an incorporated agent differently from the polymers forming the blend.

10. A process for preparing blends of miscible polymers by selecting two polymers from the group consisting of miscible polyesters and polyanhydrides determining whether the polymers are miscible by determining if phase separation occurs when the polymer blend is dissolved in a solvent in which each of the individual polymers is soluble that is miscible for at least one day at a temperature between 20 and 30° C., and selecting those blends which are formed by miscible polymers, wherein the polymer blend forms a clear single phase solution in a solvent in which each of the individual polymers is soluble, forms a uniform film when cast from solvent or melt compressed, has thermal properties selected from the group consisting of glass transition temperature and melting point that are different from the original starting polymers, and releases an incorporated agent differently from the polymers forming the blend.

11. The process of claim 10 wherein the blend is formed by melt mixing.

12. The process of claim 10 wherein the blend is formed by solvent mixing.

* * * * *